United States Patent [19]
Sanders et al.

[11] Patent Number: 5,578,037
[45] Date of Patent: Nov. 26, 1996

[54] SURGICAL GUIDE FOR FEMORAL RESECTION

[75] Inventors: Anthony Sanders, Lakeville; Ann M. Corbo, Braintree, both of Mass.

[73] Assignee: Johnson & Johnson Professional, Inc., Raynham, Mass.

[21] Appl. No.: 338,901

[22] Filed: Nov. 14, 1994

[51] Int. Cl.⁶ .................................................. A61B 17/56
[52] U.S. Cl. ............................... 606/80; 606/89; 606/102
[58] Field of Search ............................... 606/87, 89, 79, 606/80, 88, 102

[56] References Cited

U.S. PATENT DOCUMENTS

| | | | |
|---|---|---|---|
| 4,621,630 | 11/1986 | Kenna | 606/89 |
| 4,893,619 | 1/1990 | Dale et al. | 606/87 |
| 4,959,066 | 9/1990 | Dunn et al. | 606/89 |
| 5,049,149 | 9/1991 | Schmidt | 606/89 |

FOREIGN PATENT DOCUMENTS

| | | | |
|---|---|---|---|
| 415837 | 3/1991 | European Pat. Off. | 606/87 |
| 4141153 | 6/1993 | Germany | 606/87 |

OTHER PUBLICATIONS

Osteonics Corp. Product Brochure entitled "Surgical Protocol OMNIFIT® Femoral System" (1987).

*Primary Examiner*—Guy V. Tucker
*Attorney, Agent, or Firm*—William C. Geary, III; Nutter, McClennen & Fish, LLP

[57] ABSTRACT

A surgical resection guide enables a surgeon to resect a femoral neck, during a hip arthroplasty procedure, such that a femoral prosthesis can be implanted within a patient to preserve or closely approximate the anatomic center of rotation of the hip. The guide is able to be used for left or right hip arthroplasty procedures, with either anterior or posterior surgical approaches.

8 Claims, 3 Drawing Sheets

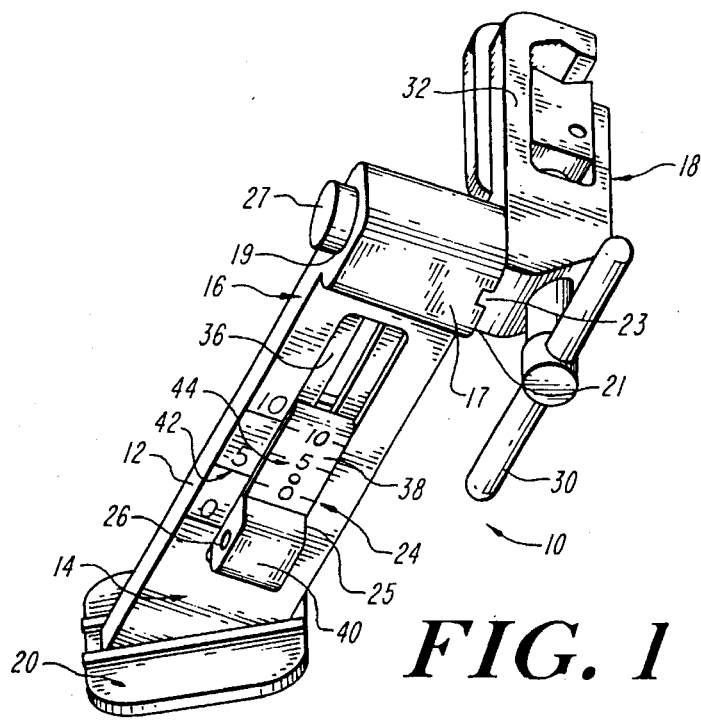
FIG. 1
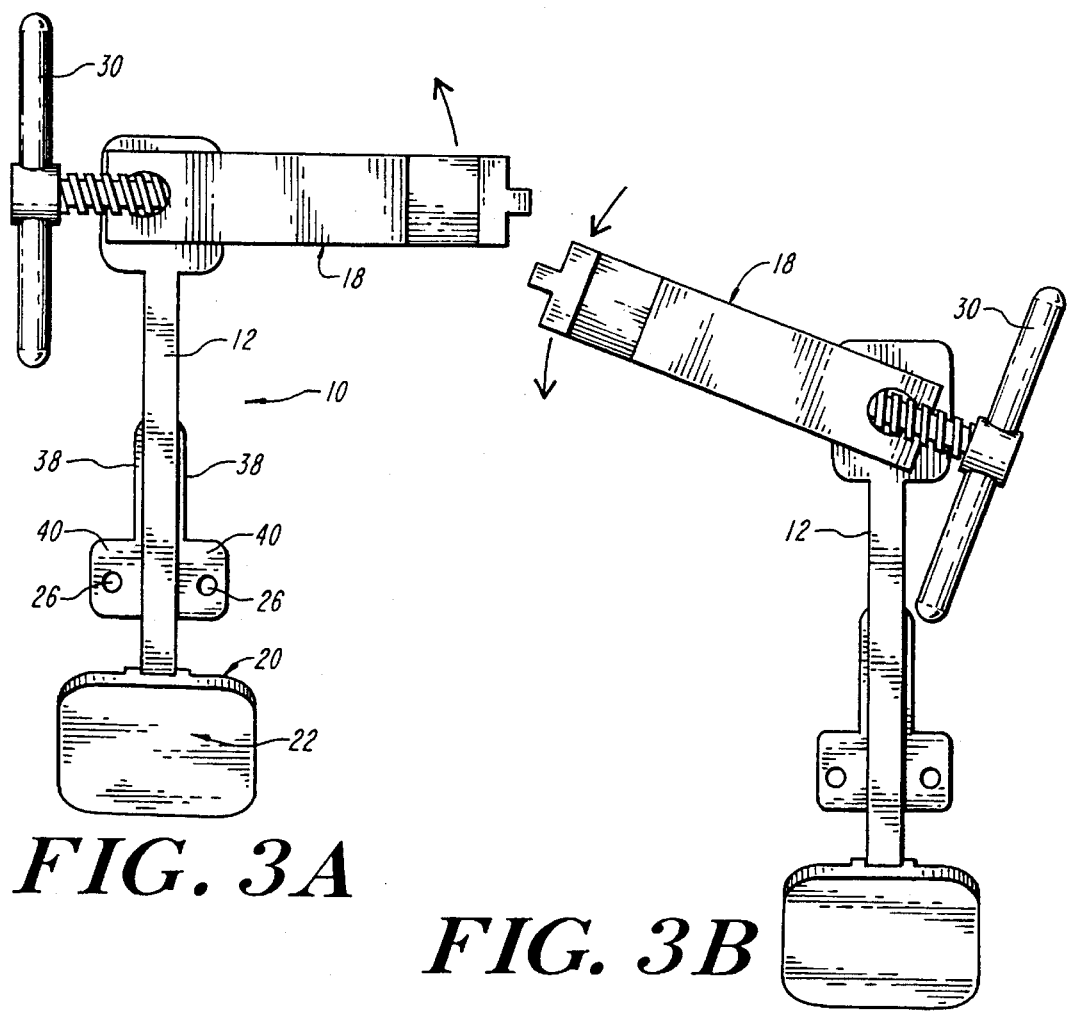
FIG. 3A
FIG. 3B

SURGICAL GUIDE FOR FEMORAL RESECTION

BACKGROUND OF THE INVENTION

This invention relates to the field of surgical instruments, and more particularly to surgical guiding instruments used in orthopedic surgery, particularly hip arthroplastic surgery, for determining an appropriate resection line through a bone.

Artificial hip joints include several components. A femoral component of a hip prosthesis comprises an elongate stem or shaft at its distal end that is affixed within the medullary canal of the femur. A proximal end of the stem includes a neck region, to which is attached a femoral head. The acetabular shell is a separate component of an artificial hip joint that is affixed within existing bone such as the acetabulum. The acetabular shell includes a cup-like region that receives the femoral head. The femoral head and the acetabular shell form an articulation couple and smooth, low frictional movement of the femoral head within the shell is essential to ensure proper functioning of the artificial hip joint. Proper positioning of the artificial hip joint is also important to proper functioning of the artificial hip joint.

Hip arthroplasty is a surgical procedure in which a natural hip joint is removed and replaced with an artificial joint. During such a surgical procedure, a diseased portion of the femur is excised, usually by cutting along a portion of the femoral neck. A prosthetic femoral component and a prosthetic femoral head replace the natural structures that are surgically removed. The positioning of the femoral component of the prosthesis is important to ensure proper fit and smooth rotation of the femoral head within its socket (i.e., the acetabular shell).

The size of the femoral prosthesis, particularly the length of the neck portion and the size of the femoral head, all vary with a patient's anatomy. For maximum success and patient comfort, orthopedic implants must simulate as closely as possible the patient's anatomy, including bone length, size, and placement within the body relative to other bones and organs. Misplacement of the implant within the bone can cause significant trauma in the surrounding bone, muscles, tendons and ligaments and can disable the patient.

It is therefore necessary to ensure that orthopedic implant structures are properly placed within a patient. In the case of a hip joint prosthesis, it is important that the anatomic center of rotation of the femoral head within the acetabular shell be located and maintained during the implantation of the replacement structure. Misplacement of the center of rotation during implantation of the femoral component of the hip joint prosthesis can affect the patient's leg length and cause potentially irreversible damage and extreme trauma to weight-bearing joints.

Femoral resection procedures involve the resection, or excision, of at least the diseased portion of the femur, typically the femoral head, by cutting at some location along the femoral neck. Difficulty arises when the resection location is determined without regard to the size of the femoral component of the hip joint prosthesis. An incorrect neck resection location can cause the prosthesis to fit improperly within the medullary canal of the femur and/or can result in misplacement of the prosthetic center of rotation relative to the anatomic center of rotation of the femur.

In current surgical techniques, the location of the resection is not rigidly instrumented to coordinate with the prosthesis to be implanted. This is a disadvantage and can adversely affect the ability to reestablish the normal anatomic center of rotation of the femoral head. Due to the fixed geometric relationship of the collar of the prosthesis to the head center, the location of the resection will ultimately determine the location of the center of rotation. Thus, with no instrumented means to control the location of the resection, it may be difficult to accurately restore the center of rotation of the femoral head.

Accordingly, there is a need for surgical instruments that will assist surgeons to resect the femoral neck at the appropriate location to reproduce within the artificial joint the hip's anatomic center of rotation.

It is therefore an object of the invention to provide an apparatus for determining the proper femoral neck resection line during hip replacement surgery. It is another object of the invention to provide improved methods of performing surgical femoral resections. A further object is to provide an apparatus that enables surgeons to accurately reproduce the center or rotation of a femoral head during hip replacement surgery. These and other objects will be apparent from the description that follows.

SUMMARY OF THE INVENTION

The invention is directed to a femoral neck resection guide that provides a surgeon with an accurate means to place the femoral neck resection plane such that it will be possible to accurately reproduce the hip's anatomic center of rotation, especially in the vertical direction along the longitudinal axis of the femur.

The resection guide comprises a rigid frame, formed of an elongate member, having distal and proximal ends disposed along a frame axis. A slidable gauge device is disposed on the frame between the distal and proximal ends of the frame to help calibrate and reference the resection guide to anatomical features of a patient's femur. A clamp is associated with the proximal end of the frame to secure the resection guide in a fixed position relative to the femur during surgical procedures. The guide also has a resection guide surface associated with a distal end of the frame. The resection guide surface provides a template against which a surgeon can deploy a reciprocating saw, or another surgical device, to define the cutting line for resecting the femoral neck.

Preferably, the clamp portion of the resection guide includes a spring loaded detent element such that the clamp can be rotated 180° about an axis transverse to the frame axis. This feature allows the same guide device to be used for both right side and left side femoral neck resection procedures.

BRIEF DESCRIPTION OF THE DRAWINGS

For a fuller understanding of the nature and objects of the invention, reference should be made to the following detailed description and the accompanying drawings.

FIG. 1 is a perspective view of a surgical resection guide according to the invention.

FIGS. 3A AND 3B are side views of the surgical resection guide illustrated in FIG. 1, showing the rotatability of the clamp portion.

DETAILED DESCRIPTION OF THE INVENTION

Figure 2:
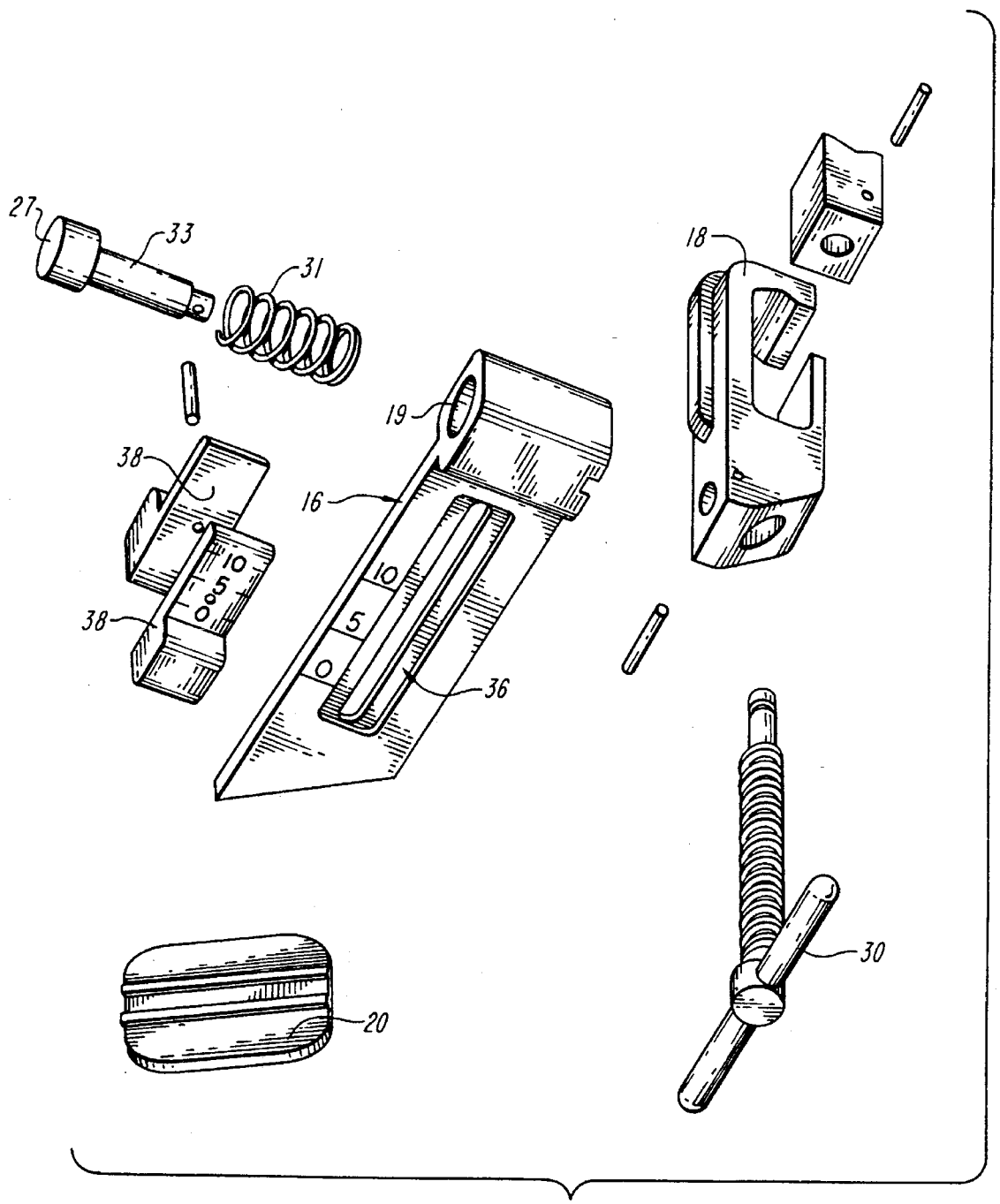
FIG. 2 is an exploded view of the resection guide illustrated in FIG. 1.

As illustrated, surgical resection guide 10 of the present invention comprises a rigid frame 12 having a distal end 14 and a proximal end 16, both of which are disposed along a longitudinal frame axis x. A guide portion 20, having a resection guide surface 22, is associated with a distal end of frame 12. The proximal end 16 of the frame 12 includes a clamp mechanism 18. An intermediate portion of the frame 12 further includes a gauge element 24 having a movable slide 25 which includes an aperture 26.

The clamp mechanism 18 is rotatably mounted to a proximal end of the frame 12 of the surgical resection guide 10. The clamp mechanism 18 preferably includes a thumbscrew 30 which can be used to selectively control the gap of a vice device 32. In use, the vice device 32 is positioned over a stationary object, such as a surgical reamer, and the thumbscrew is activated until the vice 32 secures the guide 10 to the object.

The clamp mechanism 18 further includes a collar 17 at the proximal end 16 of frame 12. The collar 17 includes a bore 19 that is oriented substantially transverse to the longitudinal axis x of the frame 12. A biasing element 31, such as a spring, is positioned within bore 19 to bias the clamp mechanism 18 into contact with a side surface 21 of frame 12. In one embodiment, the biasing element 31 is a spring that surrounds a dowel 33 positioned within bore 19, to bias the clamp mechanism in contact with the side surface 21 of the frame 12.

In a preferred embodiment, a detent mechanism 23 maintains the clamp in a desired orientation relative to the frame 12. The clamp mechanism 18 can be rotated 180° by, for example, actuating a button 27, mounted adjacent one end of bore 19, to overcome the biasing force and to cause the clamp mechanism 18 to come out of contact with side surface 21 of frame 12 and/or detent mechanism 23. Once out of contact with side surface 21 and/or detent mechanism 23, the clamp mechanism can be rotated 180° to the desired position.

As noted above, a guide portion 20 is associated with the distal end 14 of frame 12. The guide portion 20 includes a resection guide surface 22 against which a surgical tool can be positioned while resecting the femoral neck. In one embodiment, the resection guide 20 is integral with the frame 12 and is oriented at a fixed angle which determines a cutting angle. The resection guide can be oriented at virtually any angle that is desired for cutting. In a preferred embodiment, however, the guide is oriented at an angle of approximately 50° to 60°, and most preferably at about 55°. In an alternative embodiment (not illustrated), the guide can be adjustably mounted to the frame 12 so that a desired cutting angle can be selected.

The gauge device 24 is used to calibrate the guide and to position the guide and the resection guide surface 22 so that resection of the femoral neck is properly accomplished to reproduce in the hip joint prosthesis the natural center of rotation of the femoral head. As illustrated, the gauge device 24 is positioned at an intermediate location on the frame 12 of the resection guide 10. Preferably, the frame 12 includes a recessed groove 36 within which is positioned a movable slide element 25. The slide 25 includes an elongate portion 38 and a raised portion 40. The raised portion 40 preferably includes an aperture 26 within which can be positioned an indicator device 28 such as a Stienmann pin. Preferably, identical slide elements are disposed on either side of the frame 12, enabling the use of the device in both right and left side hip arthroplasty using either posterior or anterior approaches.

In a preferred embodiment, the frame includes frame calibration marks 42 while the elongate portions 38 of slide 25 include slide calibration marks 44. As explained below in detail, the calibration marks help to determine the proper resection plane of the femoral neck.

One of ordinary skill in the art will appreciate that the surgical resection guide 10 of the present invention can be manufactured in dimensions that are suitable for use in its intended surgical procedure. In one embodiment, the frame 12 is approximately 8–10 centimeters in length while the clamp spans approximately 4–8 centimeters. The clamp can be offset from the longitudinal axis of the frame by about 1–3 centimeters.

Figure 4:
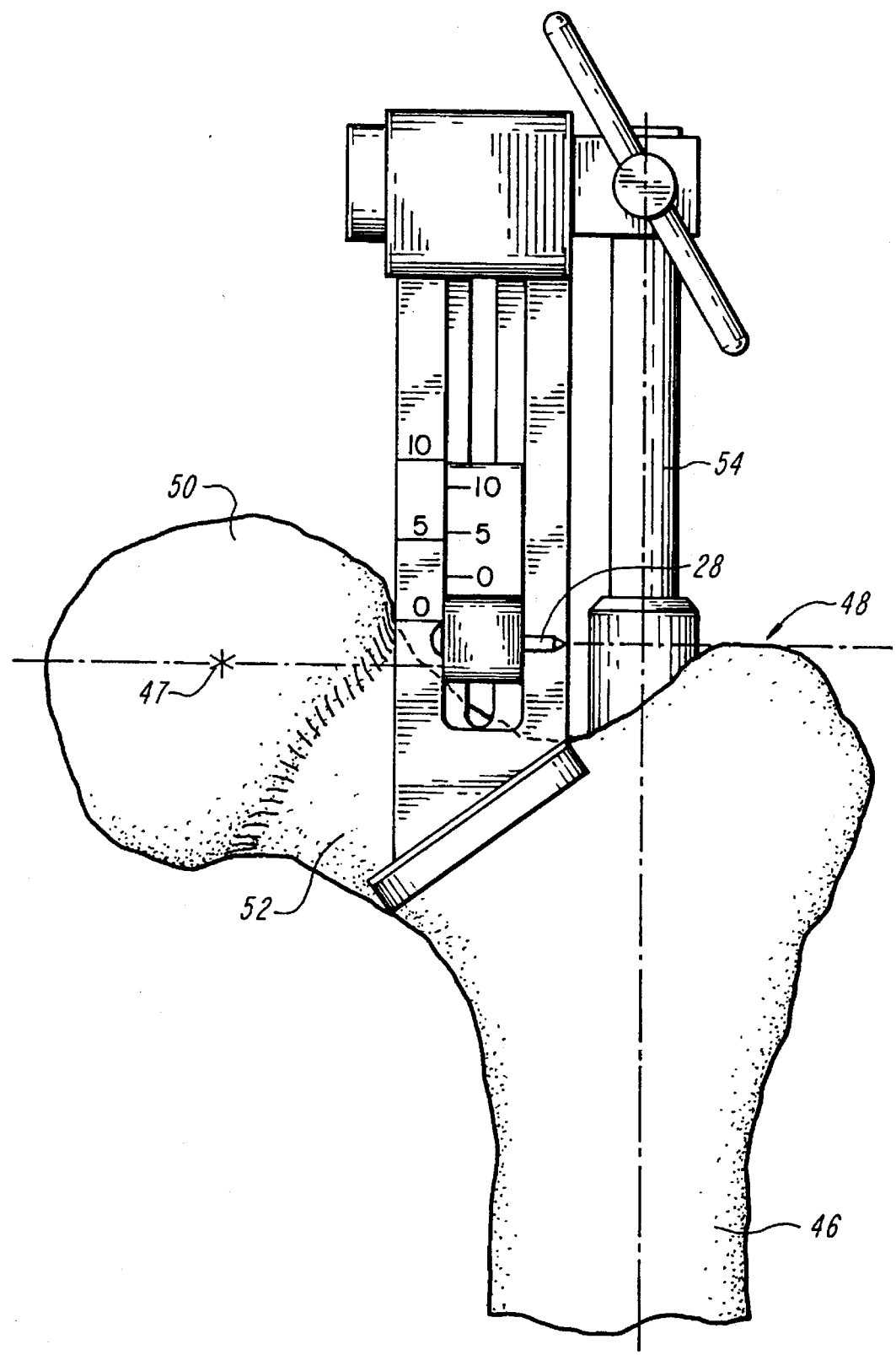
FIG. 4 is a perspective view illustrating the surgical resection guide of FIG. 1 adapted for use in hip arthroplasty surgery.

The operation of the surgical resection guide of the invention, described below, is best understood with reference to FIG. 4.

For proper use of the guide, the vertical offset between the femoral head center 47 and the superior margin of the greater trochanter 48 is to be determined. If the superior margin of the greater trochanter 48 is above the femoral head center, the distance should be recorded as a positive value in suitable units (e.g., millimeters). Conversely, if the superior margin of the greater trochanter 48 is below the femoral head center 47, the vertical offset distance should be recorded as a negative value using the appropriate units. The vertical offset value can be determined, as is well known to those having ordinary skill in the art, using an anterior/posterior femur preoperative radiograph. Next, the gauge 24 is set by aligning the proper frame calibration mark 42 with the corresponding slide calibration mark 44 based upon the femoral neck length intended to be used in the hip joint prosthesis. For example, if a 5 millimeter femoral neck length is to be used, the "+5" frame calibration mark 42 will be aligned with the "+5" calibration mark 44 on the slide element 21.

From this initial position, the guide is then offset by a distance equal to the vertical offset between the femoral head center 47 and the superior margin of the greater trochanter 48. For example, if the vertical offset value is +2 mm, the gauge 24 is adjusted by moving the slide 25 upwardly (toward the clamp) by a distance of 2 mm. Similarly, if the vertical offset value is −2 mm, the gauge 24 is adjusted by moving the slide 25 downwardly (toward the guide portion 20) by 2 ram.

During a hip arthroplasty procedure, a surgical reamer 54 is typically inserted within the medullary canal of the femur. With the surgical reamer 54 in place within the medullary canal, the surgical resection guide 10 is inserted onto the shank of the reamer 54. This is accomplished by opening the vice element 32 of the clamp mechanism 18 to a suitable size and then sliding the guide onto the shank of the reamer. The guide 10 is then positioned on the shank of the reamer 54 such that the lower indicator device 28 (e.g., a Stienmann pin) points to the superior margin of the greater trochanter 48. The clamp mechanism 18 is then fully tightened by turning thumbscrew 30 to close vice 32.

When fully tightened, the guide 10 should be in the proper position such that use of the resection guide surface 22 to guide a surgical tool, such as an oscillating saw, while resecting the femoral neck will allow the femoral component of the hip joint prosthesis to be properly seated within a patient so that the center of rotation of the femoral prosthesis will be at the same vertical position as the anatomic center of rotation. That is, the center of rotation of the hip along the longitudinal axis of the femur will be accurately restored. The offset of the center of rotation, that is the distance by which the center of rotation in the artificial hip joint is offset in an axis perpendicular to the longitudinal axis of the femur, is largely dependent on proper surgeon selection of femoral neck offset length. The device of the present invention is advantageous because it allows the surgeon to use various neck offset lengths while still obtaining correct vertical positioning of the head center.

Various modifications can, of course, be made in the use of this guide and will be apparent to those having ordinary skill in the art. For example, a surgeon can anticipate the need for a certain length extension of the femoral head (e.g., 0, 5, or 10 mm), such as based on x-ray measurements, in vivo measurements, or experience. If a 5 mm length extension is anticipated the frame calibration mark "5" is aligned with the slide calibration mark "5". Next, the clamp is positioned on the reamer 54 and the resection guide 10 is adjusted (up or down) relative to the reamer until indicator device 28 points to the center of the femoral head. The clamp mechanism 18 can then be tightened and used to assist the surgeon during femoral neck resection.

The femoral resection guide of the invention may also be used by a technique in which the surgeon first makes the assumption that the femoral head center is at the same level as the superior margin of the greater trochanter. Alternatively, it may be desired to position the center of the prosthetic femoral head so that it is level with the greater trochanter. In either case, it will not be necessary to offset the gauge by a distance equal to the vertical offset between the natural femoral center and the superior margin of the greater trochanter.

The surgical resection guide of the invention provides numerous advantages. Most importantly, the guide of this invention enables a surgeon to place the femoral head center of a hip prosthesis at a desired level. This is advantageous because the location of the femoral head center is important to the restoration of normal hip joint biomechanics and proper leg length. This instrument will also provide a surgeon the ability to make more strategic use of available femoral neck length options. For example, a surgeon may desire to use a longer femoral neck length to provide greater medial/lateral offset of the femoral head center, while still being able to achieve normal vertical positioning of the center.

Another advantage of the guide of the present invention is that a single guide can be used with both anterior and posterior surgical approaches, for both left and right hip arthroplasty procedures. This is possible due to the symmetrical design of the device and the ability of the clamp mechanism to rotate 180°.

The invention being thus disclosed, variations and modifications will occur to those having ordinary skill in the art, and such variations are intended to be within the scope of the invention as set forth in the claims appended hereto.

What is claimed is:

1. A femoral neck resection guide, comprising
   a rigid frame formed of an elongate member, the frame having distal and proximal ends disposed along a longitudinal frame axis;
   a gauge movable relative to the frame and means disposed on the frame between the distal and proximal ends of the frame for referencing the resection guide to anatomical features of a patient's femur;
   a surgical reamer having a longitudinal axis for insertion into the intramedullary canal of the fermur:
   clamp means disposed on the proximal end of the frame for securing the resection guide in a fixed position relative to the surgical reamer so that the longitudinal axis of the surgical reamer is substantially parallel to the longitudinal frame axis; and
   a resection guide surface on the distal end of the frame for defining a resection line for a femoral neck, and said gauge being movable relative to said guide surface.

2. The femoral neck resection guide of claim 1 wherein the resection guide surface extends transversely relative to the frame axis at an angle of approximately 50° to 60° relative to the longitudinal frame axis.

3. The femoral neck resection guide of claim 1 wherein the clamp means is pivotally mounted to the frame and further comprises a spring-loaded detent element to facilitate rotation of the clamp means 180° about an axis transverse to the longitudinal frame axis.

4. The femoral neck resection guide of claim 3 wherein the guide is usable during both right side and left side femoral neck resection procedures, using either anterior or posterior surgical approaches.

5. The femoral neck resection guide of claim 1 wherein the frame is adapted to be fixed relative to a patient's femur such that the longitudinal frame axis extends substantially parallel to and offset from the longitudinal axis of the femur.

6. The femoral neck resection guide of claim 1 wherein the movable gauge means includes a slidable pointer disposed within an aperture.

7. A method for defining a femoral neck resection line, comprising the steps of:
   providing a femoral neck resection guide, comprising a rigid frame formed of an elongate member, the frame having distal and proximal ends disposed along a longitudinal frame axis, a movable gauge means disposed on the frame between the distal and proximal ends of the frame for referencing the resection guide to anatomical features of a patient's fermur, clamp means disposed on the proximal end of the frame for securing the resection guide in a fixed position relative to the femur, and a resection guide surface associated with the distal end of the frame for defining a selected resection line through a femoral neck;
   referencing the resection guide to anatomical features of a patient's femur by vertically positioning the moveable gauge means relative to the rigid frame to indicate the anatomical center of rotation of the femur; and
   fixedly positioning the resection guide relative to the femur such that the frame extends substantially parallel to and offset from the longitudinal axis of the femur and such that the resection guide surface is disposed adjacent to the femoral neck to define the selected resection line through the femoral neck.

8. A method of claim 7 wherein the step of fixedly positioning includes fixedly positioning the resection guide relative to the femur by attaching the clamp means to a surgical reamer disposed within the medullary canal of a patient's femur.

* * * * *